United States Patent
Christakis et al.

(10) Patent No.: US 10,583,022 B2
(45) Date of Patent: Mar. 10, 2020

(54) STENT DELIVERY SYSTEMS WITH A RECONSTRAINING MEMBER

(71) Applicant: BOSTON SCIENTIFIC SCIMED, INC., Maple Grove, MN (US)

(72) Inventors: Laura E. Christakis, Worcester, MA (US); Colby Harris, Weston, MA (US); Gerald Fredrickson, Westford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 532 days.

(21) Appl. No.: 14/943,481

(22) Filed: Nov. 17, 2015

(65) Prior Publication Data

US 2016/0135973 A1    May 19, 2016

Related U.S. Application Data

(60) Provisional application No. 62/081,762, filed on Nov. 19, 2014.

(51) Int. Cl.
*A61F 2/966* (2013.01)

(52) U.S. Cl.
CPC ...... *A61F 2/966* (2013.01); *A61F 2002/9665* (2013.01)

(58) Field of Classification Search
CPC .. A61F 2/95; A61F 2/962; A61F 2/966; A61F 2002/9665; A61F 2002/9534
See application file for complete search history.

(56) References Cited

U.S. PATENT DOCUMENTS

| | | | |
|---|---|---|---|
| 5,238,004 A | 8/1993 | Sahatjian et al. | |
| 5,534,007 A * | 7/1996 | St. Germain | A61F 2/95 606/191 |
| 5,733,267 A | 3/1998 | Del Toro | |
| 5,749,921 A | 5/1998 | Lenker et al. | |
| 5,772,609 A | 6/1998 | Nguyen et al. | |
| 5,788,707 A | 8/1998 | Del Toro et al. | |
| 6,059,813 A | 5/2000 | Vrba et al. | |
| 6,139,510 A | 10/2000 | Palermo | |
| 6,508,803 B1 | 1/2003 | Horikawa et al. | |
| 7,285,130 B2 | 10/2007 | Austin | |
| 7,393,358 B2 | 7/2008 | Malewicz | |
| 2003/0004561 A1 * | 1/2003 | Bigus | A61F 2/95 623/1.12 |
| 2003/0114910 A1 | 6/2003 | Laakso et al. | |
| 2006/0030923 A1 * | 2/2006 | Gunderson | A61F 2/95 623/1.11 |
| 2006/0184226 A1 | 8/2006 | Austin | |
| 2007/0016280 A1 * | 1/2007 | Yacoby | A61F 2/88 623/1.11 |
| 2007/0208350 A1 * | 9/2007 | Gunderson | A61F 2/95 606/108 |
| 2011/0137396 A1 * | 6/2011 | Dorn | A61F 2/95 623/1.11 |

* cited by examiner

*Primary Examiner* — Sarah A Simpson
(74) *Attorney, Agent, or Firm* — Seager, Tufte & Wickhem, LLP

(57) ABSTRACT

Stent delivery systems and methods for making and using stent delivery systems are disclosed. An example stent delivery system may include an inner shaft. A deployment sheath may be disposed about the inner shaft. A stent may be disposed between the inner shaft and the deployment sheath. A stent reconstraining member may be secured to an inner surface of the deployment sheath and releasably secured to the stent.

14 Claims, 9 Drawing Sheets

STENT DELIVERY SYSTEMS WITH A RECONSTRAINING MEMBER

CROSS-REFERENCE TO RELATED APPLICATIONS

This application claims priority under 35 U.S.C. § 119 to U.S. Provisional Application Ser. No. 62/081,762, filed Nov. 19, 2014, the entirety of which is incorporated herein by reference.

TECHNICAL FIELD

The present disclosure pertains to medical devices, and methods for manufacturing medical devices. More particularly, the present disclosure pertains to stent delivery systems with a stent reconstraining member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a stent delivery system. The stent delivery system comprises:
an inner shaft;
a deployment sheath disposed about the inner shaft;
a stent disposed between the inner shaft and the deployment sheath; and
a stent reconstraining member secured to an inner surface of the deployment sheath and releasably secured to the stent.

Alternatively or additionally to any of the embodiments above, the stent is a laser cut metallic stent.

Alternatively or additionally to any of the embodiments above, the stent is a self-expanding stent.

Alternatively or additionally to any of the embodiments above, the stent includes a coating.

Alternatively or additionally to any of the embodiments above, the reconstraining member includes a biodegradable material.

Alternatively or additionally to any of the embodiments above, the reconstraining member includes a proximal region and a distal region, the distal region being designed to separate from the proximal region.

Alternatively or additionally to any of the embodiments above, further comprising an outer sheath disposed along an outer surface of the deployment sheath.

Alternatively or additionally to any of the embodiments above, the outer sheath has a distal end that is positioned proximally of a distal end of the deployment sheath.

Alternatively or additionally to any of the embodiments above, the reconstraining member has a proximal handle region.

Alternatively or additionally to any of the embodiments above, a pull wire is coupled to the reconstraining member and extends proximally therefrom.

Alternatively or additionally to any of the embodiments above, the reconstraining member includes a fold prior to deploying the stent at a target region.

Another example stent delivery system comprises:
an inner shaft having a distal tip, a stent loading region, and a bumper;
a self-expanding stent disposed along the stent loading region;
a foldable sheath disposed about the stent;
a deployment sheath disposed about the foldable sheath; and
wherein the foldable sheath is attached to an inner surface of the deployment sheath and is releasably attached to the stent.

Alternatively or additionally to any of the embodiments above, the foldable sheath includes a biodegradable material.

Alternatively or additionally to any of the embodiments above, the foldable sheath includes a proximal region and a distal region, the distal region being designed to separate from the proximal region.

Alternatively or additionally to any of the embodiments above, further comprising an outer sheath disposed along an outer surface of the deployment sheath, the outer sheath having a distal end that is positioned proximally of a distal end of the deployment sheath.

Alternatively or additionally to any of the embodiments above, the foldable sheath has a proximal handle region.

Alternatively or additionally to any of the embodiments above, a pull wire is coupled to the foldable sheath and extends proximally therefrom.

An example method for delivering a stent is disclosed. The method comprises:
advancing a stent delivery system through a body lumen to a position adjacent to a target;
wherein the stent delivery system comprises:
an inner shaft having a distal tip, a stent loading region, and a bumper,
a self-expanding stent disposed along the stent loading region,
a foldable sheath disposed about the stent,
a deployment sheath disposed about the foldable sheath, and
wherein the foldable sheath is attached to an inner surface of the deployment sheath and is releasably attached to the stent;
proximally retracting the deployment sheath to deploy the stent; and proximally retracting the foldable sheath.

Alternatively or additionally to any of the embodiments above, proximally retracting the deployment sheath to deploy the stent includes proximally retracting the deployment sheath to partially deploy the stent and distally advancing the deployment sheath to reconstrain the stent.

Alternatively or additionally to any of the embodiments above, proximally retracting the deployment sheath to deploy the stent further comprises repositioning the stent delivery system relative to the target and proximally retracting the deployment sheath a second time.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
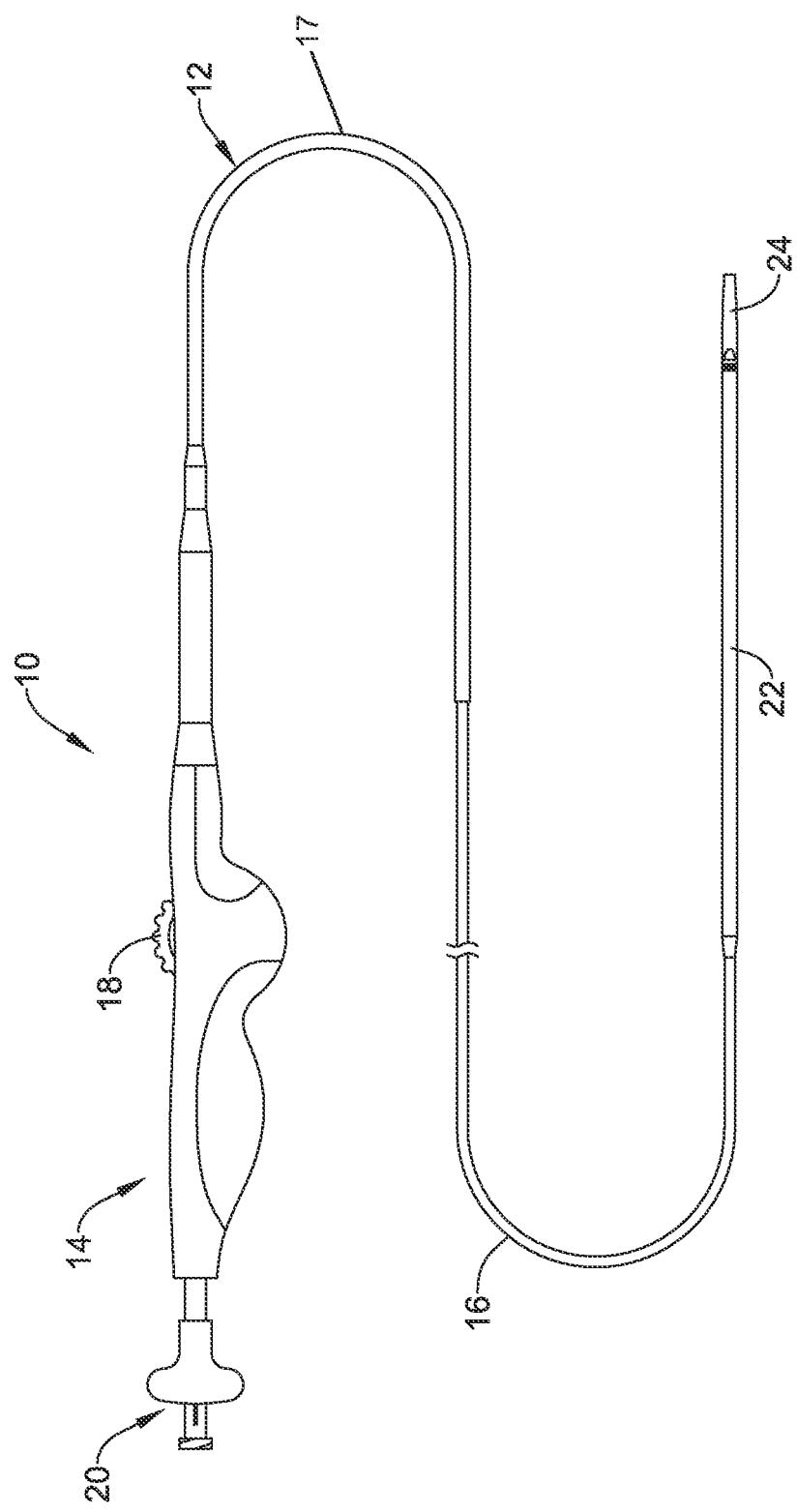
FIG. 1 is a side view of an example medical device delivery system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. System 10 may include an elongate shaft 12 and a handle 14 coupled to shaft 12. In general, system 10 may be used to deliver a suitable stent, graft, endoprosthesis or the like to an area of interest within a body lumen of a patient. The body lumen may be a blood vessel located near the heart (e.g., within or near a cardiac vessel), within a peripheral vessel, within a neurological vessel, along the biliary and/or pancreatic tract, and/or at any other suitable location. Deployment of the stent may include the proximal refraction of a retraction sheath 16, which overlies the stent. Retraction of deployment sheath 16 may include the actuation of an actuation member 18 generally disposed at handle 14. In the example illustrated in FIG. 1, actuation member 18 is a thumbwheel that can be rotated by a clinician in order to accomplish proximal refraction of deployment sheath 16. Numerous other actuation members are contemplated. In some instances, a pull handle 20 may be disposed at the proximal end of handle 14.

The components of system 10 may include other features. For example, deployment sheath 16 may have an enlarged distal end region 22. This may allow more space for a stent or the like to be contained therein during delivery. Distal end region 22 may extend to a distal tip 24 of an inner shaft (not shown in FIG. 1, can be seen in FIG. 2). Furthermore, shaft 12 may include an outer shaft or member 17. Outer shaft 17 may have a distal end that is positioned proximally of the distal end of deployment sheath 16. Other features of system 10 may include those disclosed in U.S. Pat. No. 8,784,468, the entire disclosure of which is herein incorporated by reference.

Figure 2:
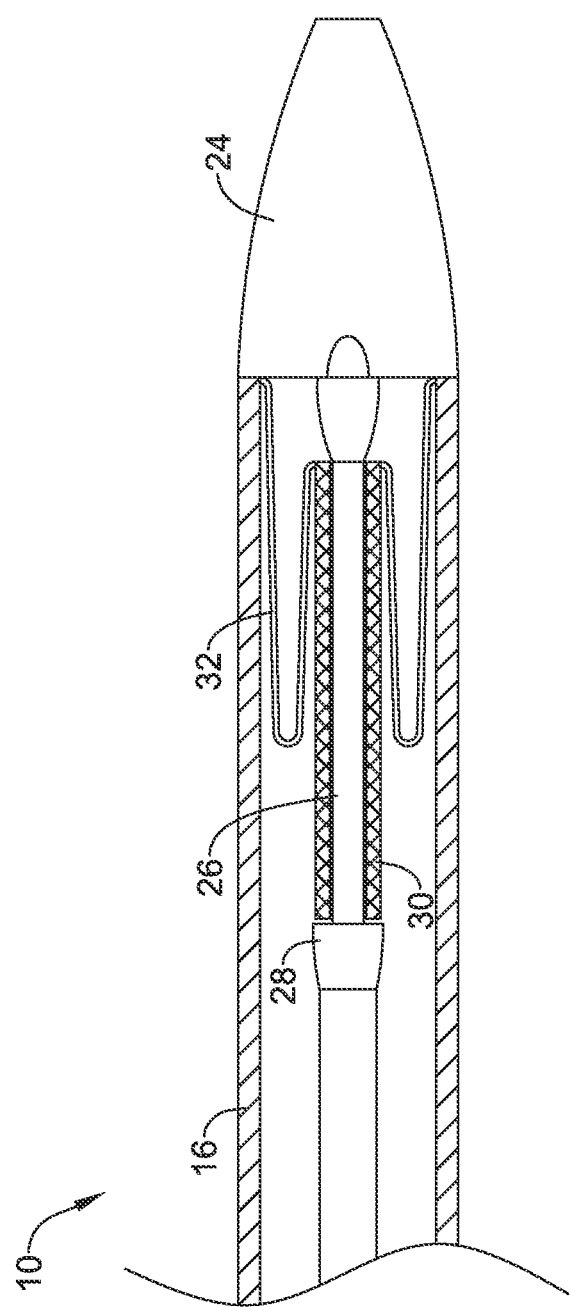
FIG. 2 is a partial cross-sectional side view of a portion of an example system.

FIG. 2 is a partial cross-sectional side view of a portion of system 10. Here it can be seen that system 10 includes an inner member or shaft 26. In at least some embodiments, inner member 26 is tubular and defines a lumen therethrough. The lumen may be a guidewire lumen or other type of lumen. A bumper 28 may be disposed along inner member 26. Bumper 28 may function as a proximal stop that may aid in limiting proximal movement of a stent 30 during deployment. In some instances, bumper 28 may take the form of a sleeve or flange coupled to the outer surface of inner member 26. In other instances, bumper 28 may be a buildup of material along inner member 26. These are just examples. Other variations are contemplated.

Stent 30 may be disposed along inner member 26. Stent 30 may take the form of a self-expanding stent. In other words, stent 30 may be formed from a shape memory material (e.g., a nickel-titanium alloy) that is designed to expand to a pre-defined shape upon exposure to a particular temperature environment. Stent 30 may be formed by laser cutting a metallic tube. In other instances, stent 30 may be formed by braiding or weaving one or more wires or tube. In still other instances, stent 30 may be formed from a polymeric material such as those disclosed herein). In still other instances, stent 30 may be a balloon expandable stent.

During delivery of stent 30, deployment sheath 16 may be proximally retracted relative to inner member 26. This uncovers a portion of stent 30 and allows stent 30 to self-expand. Often, stent 30 is deployed at a particular target location. However, in some instances, stent 30 could miss or slightly miss the target during deployment. Furthermore, deployment of stent 30 could involve the jumping or sudden movement of stent 30 to a position that is shifted relative to the target. In instances where stent 30 is deployed at a location that is deemed to be less than satisfactory, it may be desirable to relocate stent 30. However, once stent 30 begins to expand it may be more difficult to collapse and relocate stent 30.

System 10 may also include a stent reconstraining member 32. In general, stent reconstraining member 32 may be positioned between stent 30 and deployment sheath 16 and is designed to remain at least partially in contact with stent 30 during the deployment process. Because of this, stent reconstraining member 32 may allow stent 30 to be at least partially deployed within a target region and then "reconstrained" or otherwise resheathed within deployment sheath 16 so that stent 30 can be relocated or removed if desired.

In at least some instances, stent reconstraining member 32 may take the form of a sleeve of material that is attached to an inner surface of deployment sheath 16. Stent reconstraining member 32 may extend to and engage stent 30. In at least some instances, stent reconstraining member 32 is secured or otherwise attached to stent 30. The attachment may be understood to be a "detachable" or "releasable" attachment or securement. In other words, stent reconstraining member 32 may be designed to attached to stent 30 and then become detached under certain circumstances. In some instances, reconstraining member 32 may be attached to stent 30 with a suitable bond. This may include a mechanical bond, adhesive bond, thermal bond, or the like. For example, reconstraining member 32 may engage and be mechanically secured to stent 30 at the crossing points of the matrix of stent 30. When partially or fully collapsed, reconstraining member 32 remains sufficiently attached to stent 30 by virtue of being capture within the collapsed stent matrix. When stent 30 is fully expanded, the openings at the crossing points of stent 30 may enlarge so that reconstraining member 32 is released from stent 30. In other instances, the bond between stent 30 and reconstraining member 32 may remain intact until exposed to a predefined level of tensile force. Therefore, releasing reconstraining member 32 from stent 30 may occur when reaching the threshold level of the predefined tensile force so as to "release" reconstraining member 32 from stent 30.

Stent reconstraining member 32 may include one or more folds. For example, stent reconstraining member 32 may attach to the inner surface of the deployment sheath 16 adjacent the distal end of deployment sheath 16, extend proximally within deployment sheath 16 to a fold point, fold and extend back distally to a position adjacent to the distal end of stent 30. Other configurations are contemplated where stent reconstraining member 32 includes more than one fold, where the attachment points of stent reconstraining member 32 are shifted, and the like.

Figure 3:
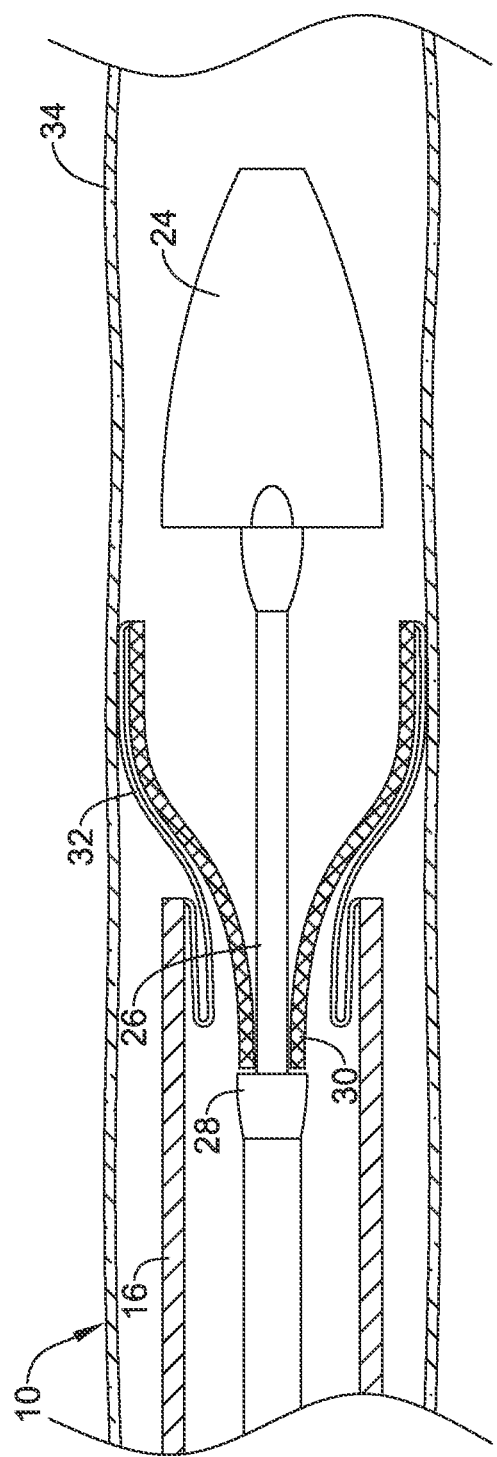
FIGS. 3-4 depict the use of an example system for deploying a stent.
Figure 4:
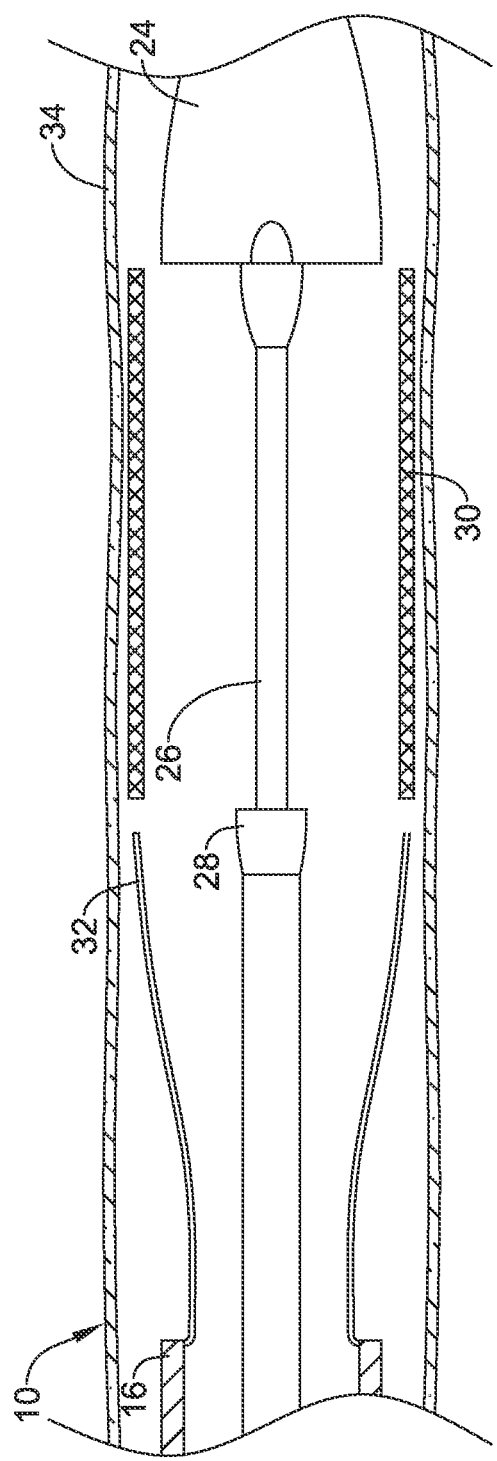

FIGS. 3-4 depict an example delivery of stent 30 to a target within a body lumen or vessel 34 (e.g., a blood vessel) using system 10. Here it can be seen that after system 10 is positioned at the desired location within vessel 34, deployment sheath 16 may be proximally retracted. When this happens, stent 30 begins to partially expand within vessel 34 as shown in FIG. 3. While stent 30 is partially expanded, stent reconstraining member 32 may remain positioned along the outer surface of stent 30 and extend like a ramp or funnel into deployment sheath 16. Because of this, if a clinician decides that stent 30 should be repositioned, deployment sheath 16 may be advanced distally to recapture or "reconstrain" stent 30 within deployment sheath 16 (e.g., system 10 would be configured as shown in FIG. 2). This may allow system 10 to be repositioned within vessel 34 to another location. Once suitably repositioned, deployment sheath 16 can be proximally retracted a second time to attempt to suitably deploy stent 30.

In addition to aiding in reconstraining and/or resheathing stent 30, reconstraining member 32 may also function as a layer of protection between stent 30 and deployment sheath 16. For example, in instances where stent 30 includes a coating, it may be desirable to reduce the amount of contact between stent 30 and deployment sheath 16. By placing reconstraining member 32 between stent 30 and deployment sheath 16, reconstraining member 32 may shield stent 30 from unwanted contact.

When the position of stent 30 within vessel 34 is determined to be satisfactory (after just one or after more than one attempt), deployment sheath 16 can be further proximally retracted to fully deploy stent 30. When doing so, stent 30 may expand within vessel 34 and be fully implanted. After this deployment, deployment sheath 16 may be further retracted to proximally "pull" stent reconstraining member 32 out from underneath stent 30 (e.g., out from between stent 30 and the wall of vessel 34) as shown in FIG. 4. In some of these and in other instances, reconstraining member 32 can be pulled out from underneath stent 30 by proximally pulling on system 10 or by another suitable mechanism. To aid in removing reconstraining member 32, reconstraining member 32 may include or be coated with a lubricious material such as those disclosed herein.

In some instances, removing reconstraining member 32 may not be necessary and/or desired. For example, when stent 30 is a bare metal or "uncoated" stent, reconstraining member 32 may not only function as an aid for reconstraining and/or resheathing stent 30, it may also function as a coating for stent 30 after deployment. In some instances, reconstraining member 32 may be biodegradable and/or bioabsorbable (e.g., reconstraining member 32 can degrade over time). In some of these and in other instances, reconstraining member 32 may include one or more therapeutic, antimicrobial, anti-inflammatory, or other type of pharmaceutical that can elute from or otherwise be delivered by reconstraining member 32. In some of these and in other embodiments, reconstraining member 32 may also help to either promote or reduce tissue ingrowth within stent 30. These are just examples. Other features, benefits, and characteristics of reconstraining member 32 are contemplated.

In addition or in the alternative, reconstraining member 32 may include materials such as polyurethanes, linear and crosslinked poly(ether/ester)s, polycaprolactone compolymers, poly(1,3-trimethylene carbonate) and copolymers, poly(polyol sebacate)s, poly(diol-citrates), poly(ester amide)s, poly vinyl alcohols plasticized with polyethylene glycols, thermoplastic elastomers, polyethylene glycol/polybutylene terephthalate, polyethylene glycol/polyethylene terephthalate, polyethylene terephthalate, polyimide, combinations thereof, and the like, or other materials as disclosed herein. In some instances, reconstraining member 32 may include a biostable material (e.g., a biostable polymer) such as those disclosed herein (e.g., polyethylene terephthalate, polyimide, etc.). These are just examples.

Figure 5:
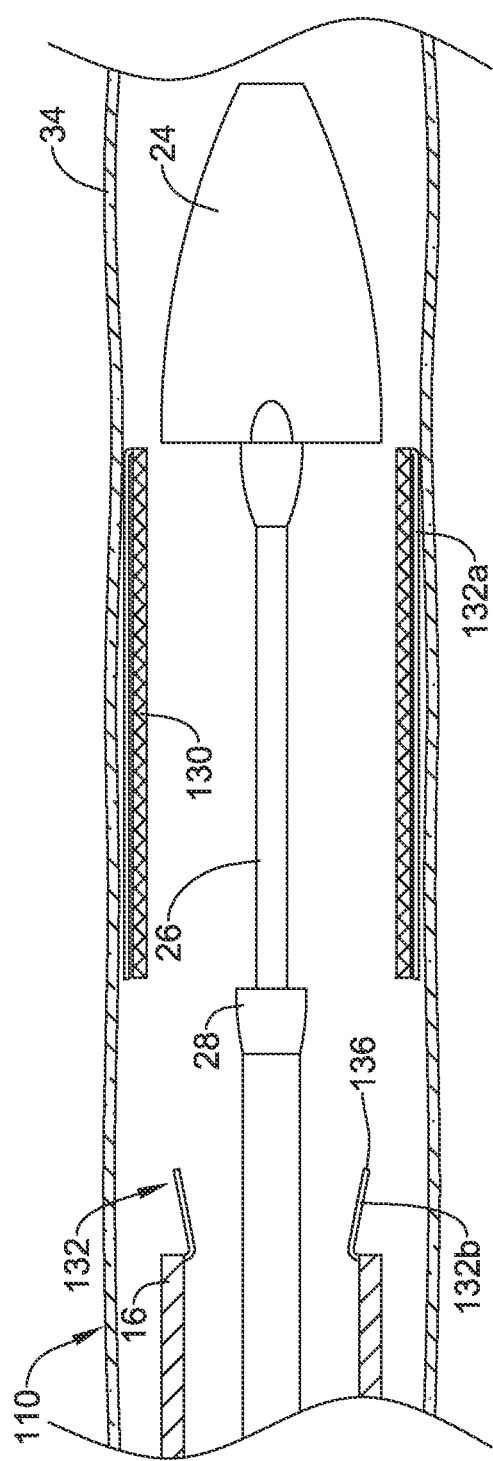
FIG. 5 depicts the use of an example system for deploying a stent.

FIG. 5 illustrates system 110 that may be similar in form and function to other systems disclosed herein and may be used to delivery stent 130. System 110 includes a severable reconstraining member 132. Thus, rather than removing reconstraining member 132 (e.g., in a manner disclosed herein for other reconstraining members), it may be desirable to "sever" or break off a portion of reconstraining member. In this example, a distal portion 132a of reconstraining member 132 can separate from the remaining portion 132b of reconstraining member 132 at a break point 136. Break point 136 may be a narrowing, thinning, perforated region, area of weakness, or the like that allows reconstraining member 132 to break at a sufficient level of force.

Figure 6:
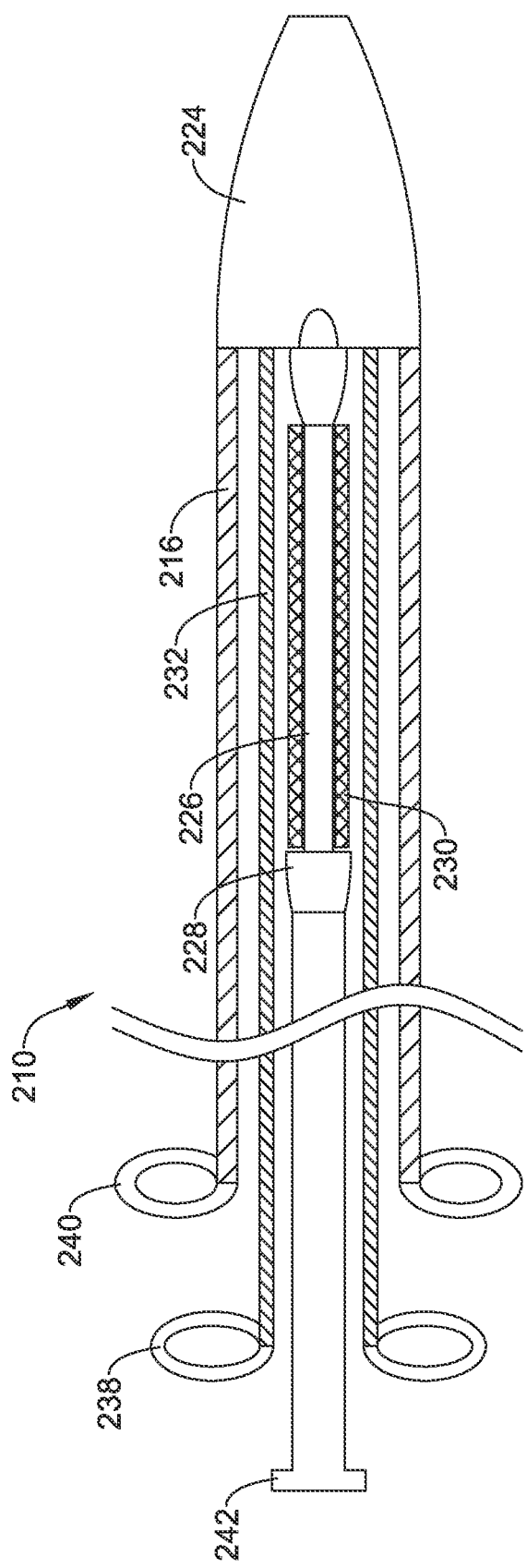
FIG. 6 is a partial cross-sectional side view of a portion of an example system.

FIG. 6 illustrates another example system 210 that may be similar in form and function to other systems disclosed herein. System 210 includes inner member 226 having distal tip 224 and bumper 228. System 210 may also include deployment sheath 216 and reconstraining member 232.

In at least some instances, reconstraining member 232 may take the form of a tubular sheath having a handle member 238 coupled thereto. Deployment sheath 216 may also include a handle member 240. Inner member 226 may also include a handle member 242. In some instances, reconstraining member 232 is free from attachment to stent 230, inner member 226, and/or deployment sheath 216. In other instances, reconstraining member 232 may be attached to stent 230 in a manner similar to how reconstraining member 32 is releasably attached to stent 30.

Figure 7:
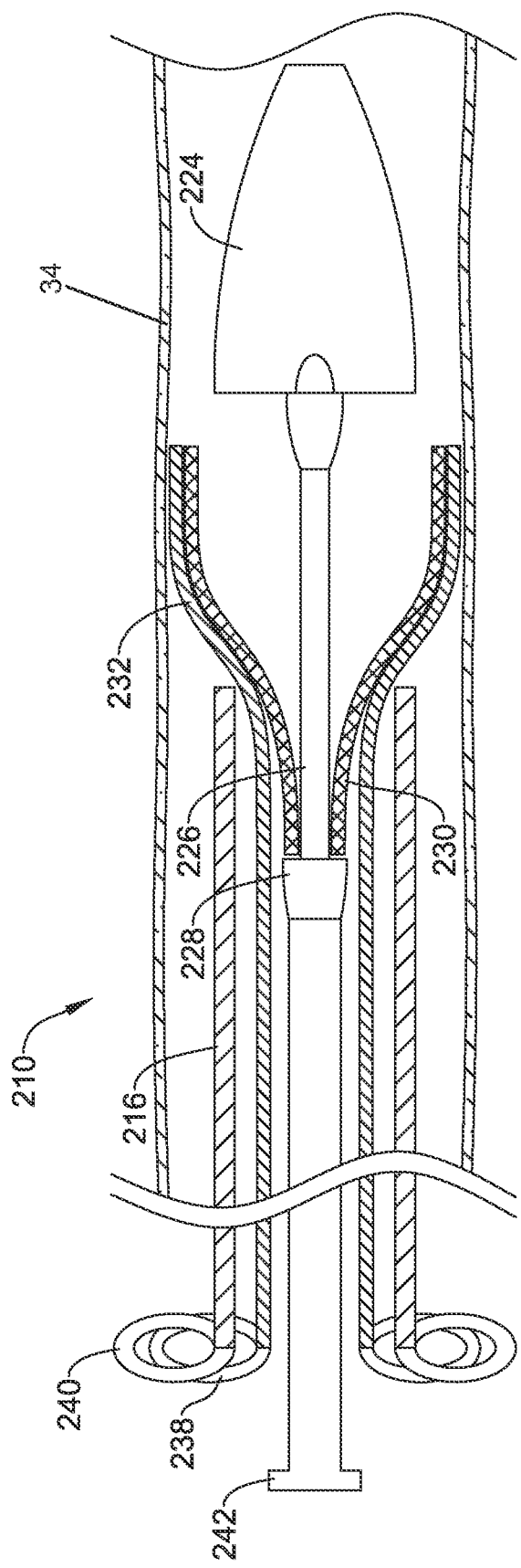
FIGS. 7-8 depict the use of an example system for deploying a stent.
Figure 8:
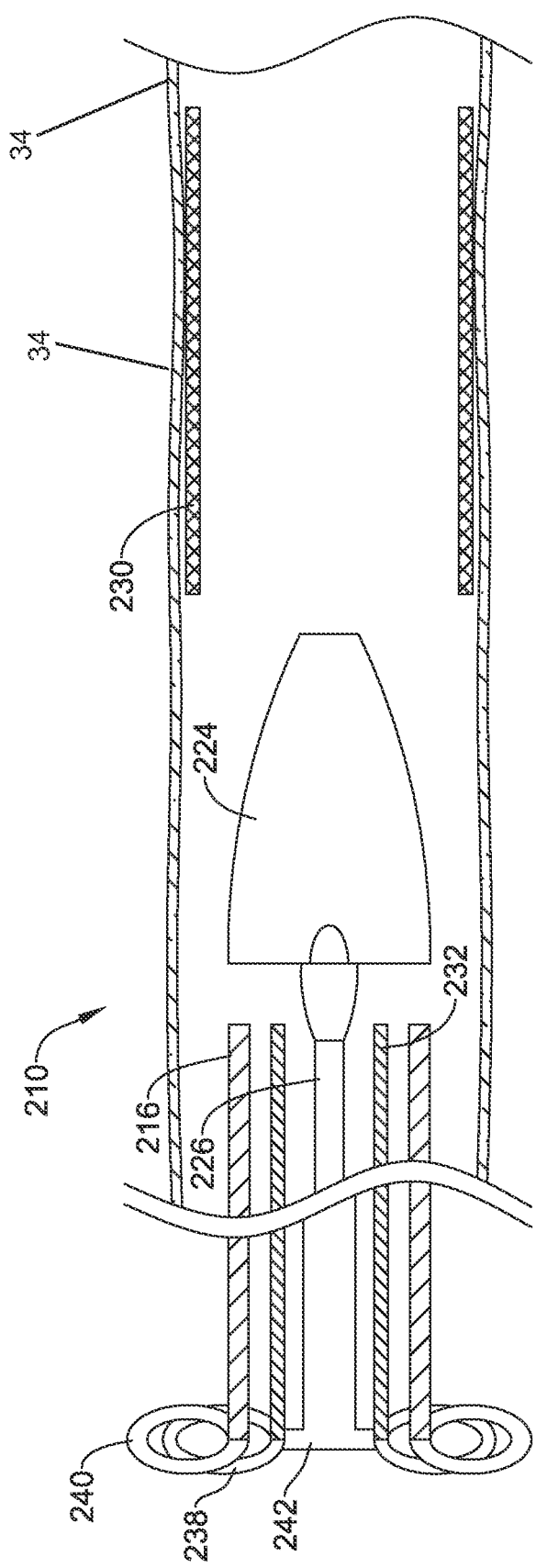

Deployment sheath 216 may be retracted (e.g., using handle member 240) to partially deploy stent 230 as shown in FIG. 7. If the position of stent 230 within vessel 34 is not satisfactory, deployment sheath 216 can be advanced distally to reconstrain/resheath stent 230. If the position of stent 230 is satisfactory, deployment sheath 216 can be pulled back further proximally to deploy stent 230 as shown in FIG. 8. When doing so, handle member 238 can be proximally retracted in order to pull reconstraining member 232 out from underneath stent 230. Alternatively, handle member 238 can be pulled proximally to sever reconstraining member 232 (e.g., in a manner similar to reconstraining member 132).

Figure 9:
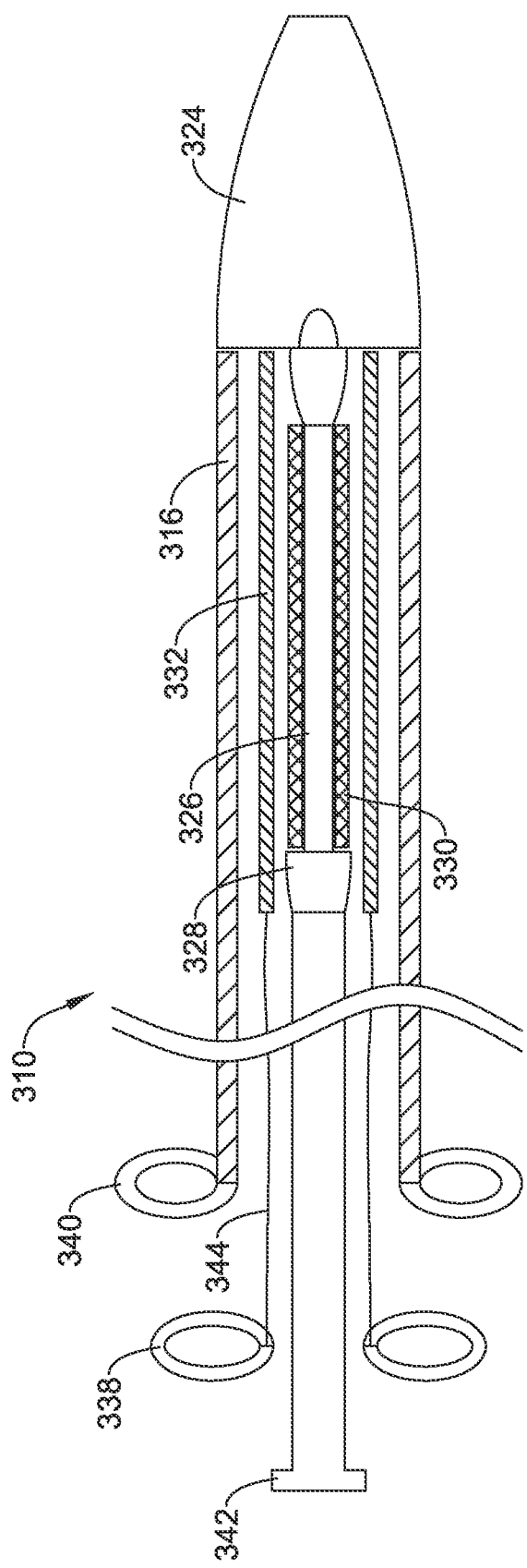
FIG. 9 is a partial cross-sectional side view of a portion of an example system.

FIG. 9 illustrates another example system 310 that may be similar in form and function to other systems disclosed herein. System 310 includes inner member 326 having distal tip 324 and bumper 328. System 310 may also include deployment sheath 316 and reconstraining member 332. Deployment sheath 316 may also include handle member 340. Inner member 326 may also include handle member 342.

In at least some instances, reconstraining member 332 may take the form of a tubular sheath having a pull wire 344 extending proximally therefrom to handle member 338. Reconstraining member 332 may be pulled out from underneath stent 330 using handle member 338. Alternatively, handle member 338 can be pulled proximally to sever reconstraining member 332 (e.g., in a manner similar to reconstraining member 132).

The materials that can be used for the various components of system 10 (and/or other systems disclosed herein) may include those commonly associated with medical devices. For simplicity purposes, the following discussion makes reference to shaft 12, deployment sheath 16, and inner member 26. However, this is not intended to limit the invention as the discussion may be applied to other similar members and/or components of members or systems disclosed herein.

Shaft 12, deployment sheath 16, and inner member 26, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12, deployment sheath 16, and inner member 26 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make shaft 12, deployment sheath 16, and inner member 26, in a manner that would impart a degree of MRI compatibility. For example, shaft 12, deployment sheath 16, and inner member 26, or portions thereof, may be made of a material that does not substantially distort the image and create substantial artifacts (artifacts are gaps in the image). Certain ferromagnetic materials, for example, may not be suitable because they may create artifacts in an MRI image. Shaft 12, deployment sheath 16, and inner member 26, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form shaft 12, deployment sheath 16, and inner member 26, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® and/or GRILAMID® TR55-LX available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery system, comprising:
  an inner shaft;
  a deployment sheath disposed about the inner shaft;
  a stent disposed radially between the inner shaft and the deployment sheath; and
  a reconstraining member, the reconstraining member includes a first end secured to an inner surface of the deployment sheath adjacent to a distal end of the deployment sheath and a free terminal end releasably secured to a distal end region of the stent;
  wherein the free terminal end is free from fixed attachment to any other component of the stent delivery system, and wherein the free terminal end of the reconstraining member is capable of extending distally beyond a distal end of the deployment sheath.

2. The stent delivery system of claim 1, wherein the stent is a laser cut metallic stent.

3. The stent delivery system of claim 1, wherein the stent is a self-expanding stent.

4. The stent delivery system of claim 1, wherein the stent includes a coating.

5. The stent delivery system of claim 1, wherein the reconstraining member includes a biodegradable material.

6. The stent delivery system of claim 1, further comprising an outer sheath disposed along an outer surface of the deployment sheath.

7. The stent delivery system of claim 6, wherein the outer sheath has a distal end that is positioned proximally of a distal end of the deployment sheath.

8. The stent delivery system of claim 1, wherein the reconstraining member includes a fold prior to deploying the stent at a target region.

9. A stent delivery system, comprising:
an inner shaft having a distal tip, a stent loading region, and a bumper;
a self-expanding stent disposed along the stent loading region;
a foldable sheath disposed about the stent;
a deployment sheath disposed about the foldable sheath;
wherein the deployment sheath is designed to shift between a first configuration where the deployment sheath overlies the self-expending stent and a deployment configuration where the deployment sheath is proximally retracted to deploy the self-expending stent; and
wherein the foldable sheath includes a first end attached to an inner surface of the deployment sheath adjacent to a distal end of the deployment sheath, wherein the foldable sheath further includes a free end defined at a terminus of the foldable sheath that is free from attachment to any other component of the stent delivery system when the deployment sheath is in the deployment configuration, and wherein the free end is releasably attached to a distal end region of the stent.

10. The stent delivery system of claim 9, wherein the foldable sheath includes a biodegradable material.

11. The stent delivery system of claim 9, further comprising an outer sheath disposed along an outer surface of the deployment sheath, the outer sheath having a distal end that is positioned proximally of a distal end of the deployment sheath.

12. A method for delivering a stent, the method comprising:
advancing a stent delivery system through a body lumen to a position adjacent to a target;
wherein the stent delivery system comprises:
an inner shaft having a distal tip, a stent loading region, and a bumper,
a self-expanding stent disposed along the stent loading region,
a foldable sheath disposed about the stent,
a deployment sheath disposed about the foldable sheath, and
wherein the foldable sheath includes a first end attached to an inner surface of the deployment sheath adjacent to a distal end of the deployment sheath, wherein the foldable sheath further includes a free terminal end that is free from fixed attachment to any other component of the stent delivery system, and wherein the free end is releasably attached to a distal end region of the stent;
proximally retracting the deployment sheath to deploy the stent; and
proximally retracting the foldable sheath.

13. The method of claim 12, wherein proximally retracting the deployment sheath to deploy the stent includes proximally retracting the deployment sheath to partially deploy the stent and distally advancing the deployment sheath to reconstrain the stent.

14. The method of claim 13, wherein proximally retracting the deployment sheath to deploy the stent further comprises repositioning the stent delivery system relative to the target and proximally retracting the deployment sheath a second time.

* * * * *